United States Patent [19]

Moffett et al.

[11] Patent Number: 5,224,923
[45] Date of Patent: Jul. 6, 1993

[54] INFANT INCUBATOR

[75] Inventors: Joseph J. Moffett, Furlong; James R. Grosholz, New Hope, both of Pa.

[73] Assignee: Air-Shields, Inc., Hatboro, Pa.

[21] Appl. No.: 799,711

[22] Filed: Nov. 26, 1991

Related U.S. Application Data

[63] Continuation of Ser. No. 499,091, Mar. 26, 1990, abandoned.

[51] Int. Cl.⁵ .............................................. A61G 11/00
[52] U.S. Cl. ........................................................ 600/22
[58] Field of Search ..................................... 606/21, 22

[56] References Cited

U.S. PATENT DOCUMENTS

| | | | |
|---|---|---|---|
| 2,366,630 | 1/1945 | Kreiselman | 600/22 |
| 2,633,842 | 4/1953 | Higgs | 600/22 |
| 3,076,451 | 2/1963 | Stoner | 600/22 |
| 3,084,492 | 4/1963 | Dorsak et al. | 600/22 |
| 3,187,744 | 6/1965 | Dorsak et al. | |
| 3,335,713 | 3/1967 | Grosholz et al. | |
| 3,464,388 | 4/1969 | Stout | 600/22 |
| 3,529,590 | 9/1970 | Grosholz | |
| 3,821,947 | 7/1974 | Schossow | |
| 4,161,727 | 7/1979 | Pickering | |
| 4,346,701 | 8/1982 | Richards | 128/200 |
| 4,356,967 | 11/1982 | Lunick | |
| 4,361,137 | 11/1982 | Grosholz | |
| 4,572,427 | 2/1986 | Selfridge et al. | |
| 4,606,299 | 8/1986 | Grumbach | |
| 4,617,912 | 10/1986 | Beer et al. | |
| 4,701,415 | 10/1987 | Dutton et al. | |
| 4,796,605 | 1/1989 | Sasaki et al. | |

FOREIGN PATENT DOCUMENTS 2944508 3/1979 Fed. Rep. of Germany .

Primary Examiner—Lee S. Cohen
Assistant Examiner—Samuel Gilbert
Attorney, Agent, or Firm—Ratner & Prestia

[57] ABSTRACT

An infant incubator having structure for humidifying filtered inlet air prior to the filtered inlet air being introduced into the air circulation path through which air is introduced into the incubator hood and recirculated upon leaving the incubator hood.

14 Claims, 3 Drawing Sheets

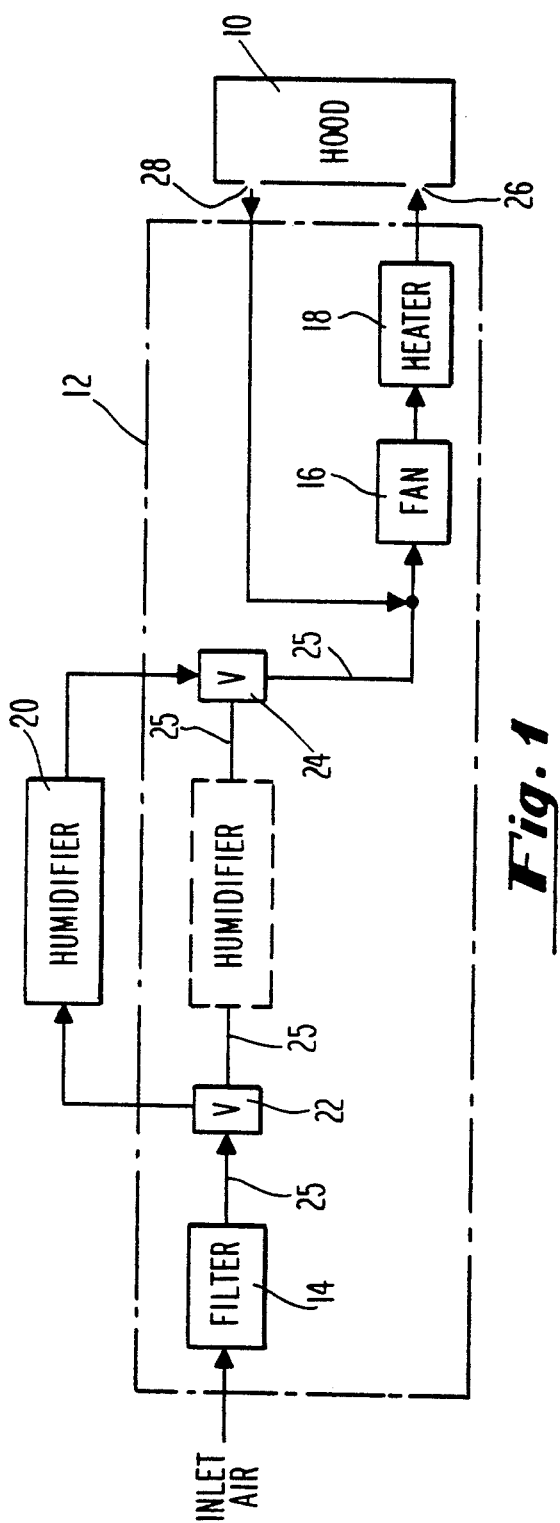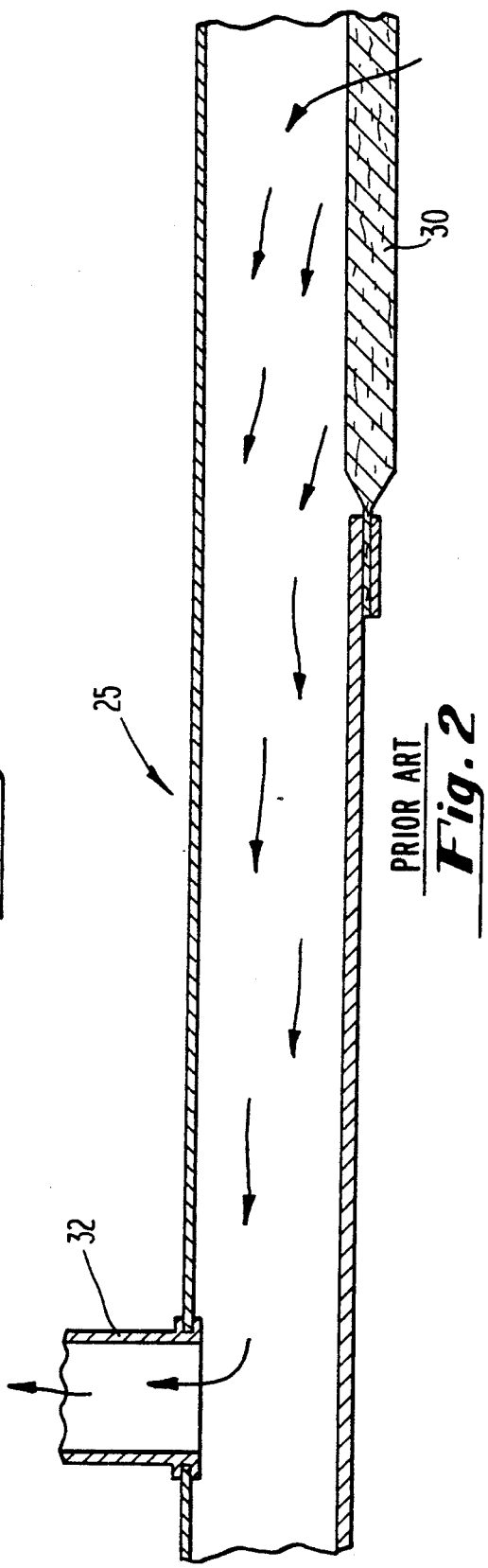

![5,224,923]

INFANT INCUBATOR

This application is a continuation of application Ser. No. 07/499,091 filed Mar. 26, 1990, now abandoned.

TECHNICAL FIELD

The present invention relates, in general, to infant incubators and, in particular, to an infant incubator having a humidifier arranged to greatly reduce or eliminate entirely the tendency, if any, of air borne contaminants affecting the quality of the air flowing through the area in which an infant is resting.

BACKGROUND OF THE INVENTION

Generally, inlet air to an infant incubator is filtered before the air enters the circulation path which extends through the hood area in which an infant is maintained and treated. Typically, the filtered air is drawn by a fan in the circulation path and conducted into the hood through a first passage. The air leaves the hood through a second passage and is conducted back to the first passage for recirculation through the hood. A heater and a humidifier are located in the air circulation path, so that the air which is introduced into the hood has the proper temperature and humidity.

The hood of an infant incubator usually is arranged with arm ports and a door to permit access to the infant if the need arises to treat the infant or to position sensors, probes and the like on the infant. When personnel attending an infant open the hood door or place their arms through the arm ports, contaminants can be introduced from the hands of such personnel and, to a lesser extent, from the environment outside the incubator.

Many users of infant incubators have the perception that such contaminants, which become airborne and enter the air circulation path, are the origin of airborne bacteria formed in the reservoir of the humidifier as the air flow with the contaminants passes through the humidifier, whereby the infant is exposed to this bacteria. Although this perception has not been substantiated, many users who have this perception, nevertheless, do not make use of the humidifier, for example, leaving the reservoir empty. Instead, they employ external humidifiers which introduce filtered or unfiltered, humidified air directly into the hood of the incubator. If the incoming humidified air from an external humidifier is not filtered appropriately, this air can carry its own variety of airborne pathogens if the humidifier reservoir is not rigorously maintained.

Such external humidifiers have a number of shortcomings. First, they require a source of pressurized gas (oxygen, air or oxygen/air mixture) to force humidified air into the incubator hood. Second, provision must be made for passing through the hood, tubing and conduits through which the humidified air is conducted into the hood. Third, the presence of such tubing and conduits can impede the maintenance and treatment of an infant within the hood. Fourth, tubing and conduits leading into the incubator hood have a propensity for a temperature drop across their lengths which can result in water vapor condensing back into a liquid state. Water in the tubing and conduits can be absorbed by linens in the incubator, thus increasing the possibility of bacteria colonization in both the tubing and conduits and the absorbent materials in the incubator. Fifth, external humidifiers generally are mounted on IV poles and the like which take up space in already crowded nurseries.

SUMMARY OF THE INVENTION

Accordingly, an infant incubator constructed in accordance with the present invention includes a hood and a base upon which the hood is mounted. Also included are first air passage means extending between first and second openings into the space defined by the hood for conducting air flow into this space through the first opening and for conducting air flow from the space within the hood through the second opening and to the first opening. This infant incubator further includes second air passage means opening to the atmosphere outside the incubator for receiving inlet air and means within the second air passage means for filtering inlet air. Also included are means for humidifying filtered inlet air and for conducting humidified filtered inlet air to the first air passage means and means for drawing humidified filtered inlet air into the first air passage means and for circulating air flow through the hood and the first air passage means.

BRIEF DESCRIPTION OF THE DRAWINGS

FIG. 1 is a schematic block diagram of an infant incubator constructed in accordance with the present invention;

FIG. 2 is a sectional view of a portion of the air inlet line of a commercially available infant incubator.

DETAILED DESCRIPTION OF THE INVENTION

Figure 3:
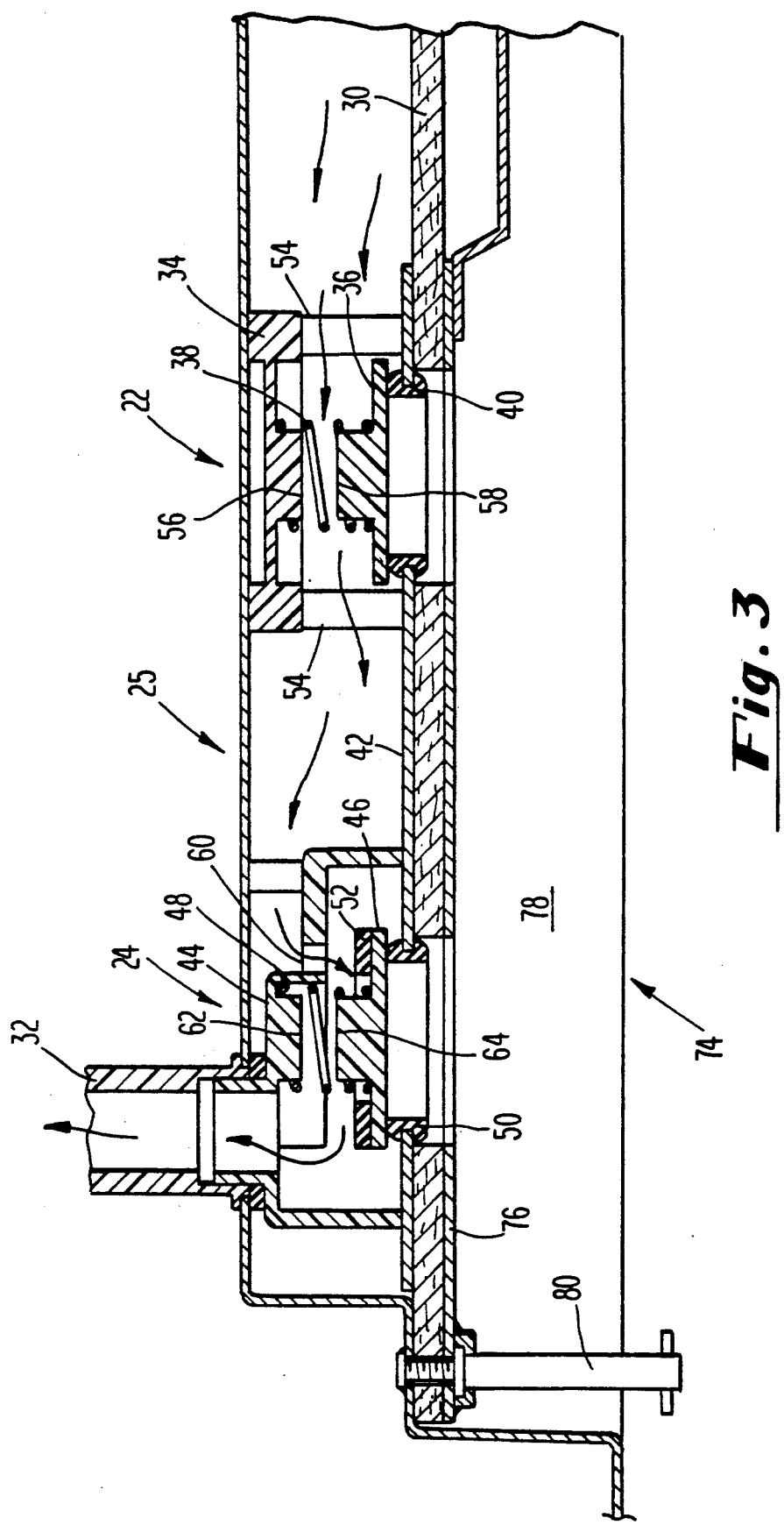
FIGS. 3 and 4 are sectional views which illustrate the manner in which the air inlet line of the infant incubator of FIG. 2 can be modified to selectively place a humidifier in the air flow path of filtered inlet air in accordance with the present invention.

An infant incubator, constructed in accordance with the present invention and illustrated schematically in FIG. 1, includes a hood 10 and a base upon which the hood is mounted. The base is represented in FIG. 1 by the dot-dash box identified by reference numeral 12 and contains an inlet air filter 14, a fan 16, a heater 18 and air passages for conducting filtered inlet air to the hood and recirculating air from the hood. U.S. Pat. No. 3,335,713 is incorporated herein by reference to supplement the disclosure of an incubator hood mounted on a base which contains various components, except for a humidifier.

An infant incubator, constructed in accordance with the present invention, also includes means for humidifying the filtered inlet air before it reaches the air circulation path. Such means include a humidifier 20 and a pair of valves 22 and 24 which divert filtered inlet air from the air passage between the valves to the humidifier when humidification of the filtered inlet air is desired. Humidifier 20 and its associated air passages, in effect, form a bypass to the air inlet line 25. This arrangement of the humidifier is particularly suited for adapting certain types of infant incubators already in service to incorporate the present invention. In an alternate arrangement of the present invention, shown by the dashed lines in FIG. 1, the humidifier can be located in the air inlet line 25 and without valves 22 and 24.

In operation, inlet air is filtered by filter 14 and the filtered inlet air is diverted by valve 22 to humidifier 20 where it is humidified to the desired extent. The humidified air is conducted through valve 24 to air passage means which extend between first and second openings 26 and 28 into the space defined by hood 10. The air passage means conduct air flow into hood 10 through opening 26 and conduct air flow from the hood through opening 28 back to opening 26. Fan 16, located in the air passage means, draws the humidified filtered inlet air to the air passage means and circulates air through the hood and the air passage means. Hood 10 is not an air-tight container. Rather, air, equal in volume to the air taken in at the air inlet, exits from the hood either by leakage at joints or seams in the incubator construction or through openings provided for the purpose of letting air escape. Heater 18, also located in the air passage means, heats the air introduced into the hood to the proper temperature.

It is important to note that the air is not humidified by humidifying apparatus located in the air circulation path. Consequently, air borne contaminants, if any, introduced in hood 10 have no water reservoir in which to collect and form bacteria which might become air borne and enter the hood when the air is circulated back into the hood. Rather, filtered inlet air is humidified upstream of the air circulation path, so that any contaminants introduced in hood 10 do not collect in the humidifier. For incubators in service having humidifying units in the air circulation path, this result can be achieved simply by leaving the humidifier reservoir empty which, as indicated above, is the way many users operate such equipment when external humidifiers are used. This is represented in FIG. 1 by the absence of a humidifier in the air circulation path.

Thus, the present invention, as depicted schematically in FIG. 1, provides an effective and practical answer to the unsubstantiated perception of many users of incubators that contaminants introduced in the hood of the incubator result in air borne bacteria circulated into the hood. The solid line arrangement of humidifier 20, whereby the humidifier forms a bypass to the air inlet line, is particularly useful in retrofitting incubators in service to achieve the desired result.

Referring to FIG. 2, which is a sectional view of a portion of the air inlet line 25 of a commercially available infant incubator, inlet air, shown by the arrows, enters the incubator through a filter pad 30. The filtered inlet air flows along air inlet line 25 and through a coupling 32 to the circulation path which is not shown in FIG. 2 but is shown in FIG. 1. There is no valve, such as valve 24, through which the humidified filtered inlet air passes from air inlet line 25 to the air circulation path.

Figure 4:
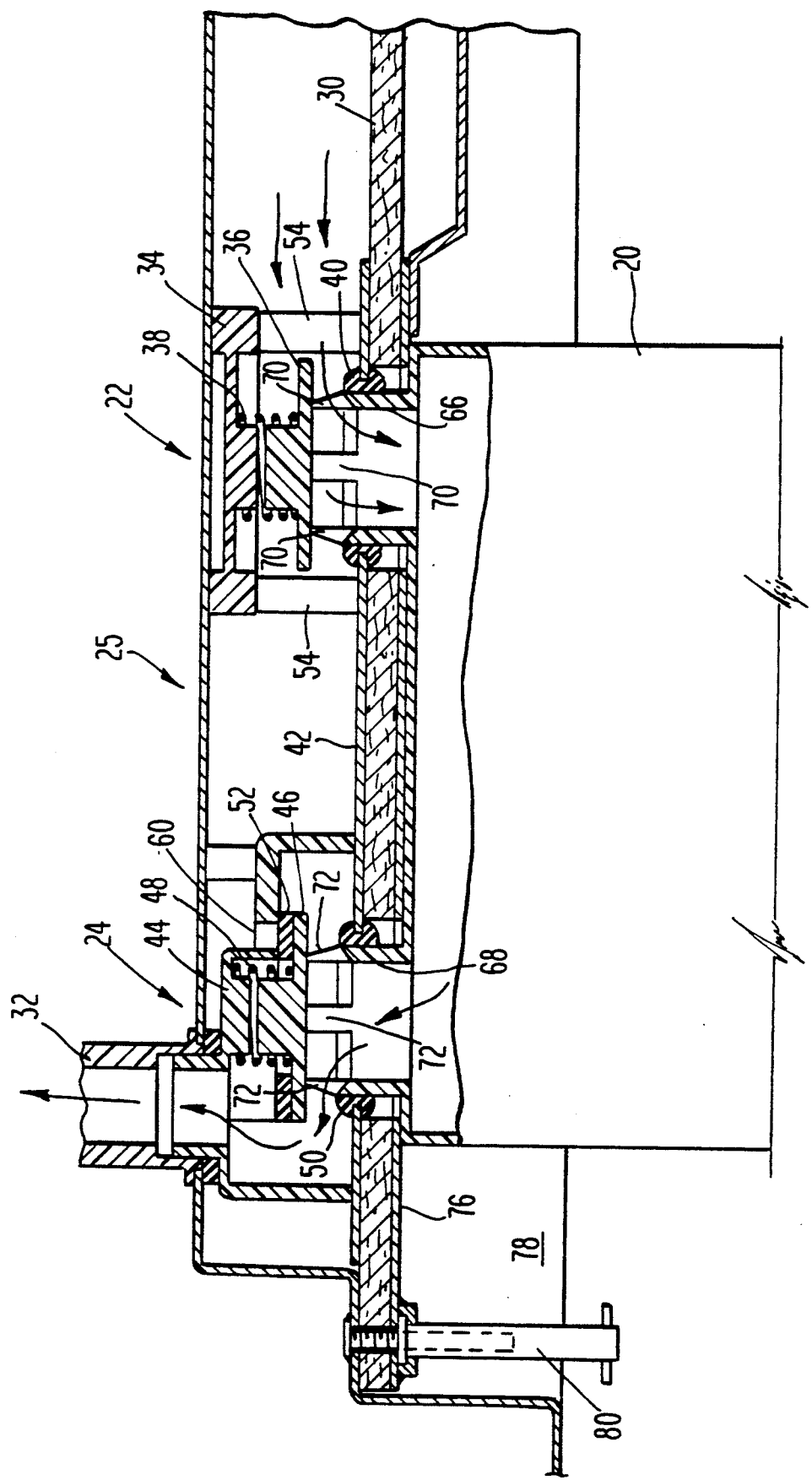

FIGS. 3 and 4, which are sectional views, illustrate the manner in which air inlet line 25 of FIG. 2 can be modified to selectively place a humidifier in the air flow path of the filtered inlet air as shown schematically in FIG. 1. FIG. 3 illustrates the air inlet line before the humidifier is introduced, while FIG. 4 illustrates the humidifier in place.

Referring to FIGS. 3 and 4, valve 22 of FIG. 1 is composed of a base 34 fixed in position within air inlet line 25, a cap 36 movable transverse to air inlet line 25, and a spring 38 which urges cap 36 against a sealing grommet 40 fitted in a first opening in a wall 42 of air inlet line 25. Valve 24 of FIG. 1 is composed of a base 44 fixed in position within air inlet line 25, a cap 46 movable transverse to air inlet line 25, a spring 48 which urges cap 46 against a sealing grommet 50 fitted in a second opening in wall 42, and a sealing ring 52 which is carried on movable cap 46.

With valves 22 and 24 as shown in FIG. 3, namely without the humidifier installed, filtered inlet air flows through valve 22, air inlet line 25 and valve 24 to coupling 32 and the air circulation path. In particular, base 34 of valve 22 has three legs 54 (only two are shown in FIGS. 3 and 4). Filtered inlet air flows into and through valve 22 and then into and through valve 24 by passing through an opening 60 in base 44 of valve 24. After passing through valve 24, the filtered inlet air passes through coupling 32 to the air circulation path. With caps 36 and 46 of valves 22 and 24, respectively, pressed against sealing grommets 40 and 50, respectively, the two openings in wall 42 of air inlet line 25 are sealed.

When humidifier 20 is installed, as shown in FIG. 4, an inlet port coupling 66 to the humidifier and an outlet port coupling 68 from the humidifier engage caps 36 and 46, respectively, of valves 22 and 24, respectively, to move caps 36 and 46 against the action of springs 38 and 48, respectively, and away from sealing grommets 40 and 50, respectively. Inlet port coupling 66 and outlet port coupling 68 each are arranged with three prongs 70 and 72, respectively. This permits filtered inlet air to enter humidifier 20 through inlet port coupling 66 and humidified air to leave the humidifier through outlet port coupling 68. The humidified air passes through coupling 32 to the air circulation path. With the humidifier installed, unhumidified filtered inlet air continues to pass through valve 22. However, as shown in FIG. 4, sealing ring 52, carried on cap 46, seals opening 60 in base 44 to close valve 24, thereby preventing unhumidified filtered inlet air from flowing to coupling 32.

FIGS. 3 and 4 illustrate other modifications to the air inlet line of FIG. 2 besides those already described. Filter pad 30 is longer and extends beyond the outlet from the humidifier, with openings in the filter pad at the inlet to the humidifier and the outlet from the humidifier. A member 74 having a vertical wall 76 and a base 78 serves to clamp filter pad 30 in place between wall 42 and wall 76 and as a support surface for the humidifier on base 78. Member 74 is mounted on air inlet line 25 by suitable means, such as a stud arrangement 80.

A humidifier which is particularly suited for incorporation in an infant incubator constructed in accordance with the present invention is described, illustrated and claimed in a copending application by Kenneth G. Miller and James R. Grosholz filed concurrently with this application and entitled "Infant Incubator Humidifier." This copending application is incorporated by reference as if its drawings and text were fully included herein. However, it will be apparent to those skilled in the art that the present invention can incorporate other types of humidifiers and, as indicated by FIG. 1 and the associated text, the present invention is applicable to infant incubators in which the humidifier is permanently installed.

The foregoing has set forth exemplary and preferred embodiments of the present invention. It will be understood, however, that various alternatives will occur to those of ordinary skill in the art without departure from the spirit and scope of the present invention.

What is claimed is:
1. An infant incubator comprising:
    a hood;
    a base upon which said hood is mounted;
    first air passage means extending between first and second openings into said hood for conducting air flow into said hood through said first opening and for conducting air flow leaving said hood through said second opening and to said first opening;

second air passage means opening to the atmosphere for receiving inlet air from the atmosphere;

means within said second air passage means for filtering inlet air;

means upstream from said first air passage means for selectively humidifying filtered inlet air and for selectively conducting humidified filtered inlet air or unhumidified filtered inlet air to said first air passage means;

and means within said first air passage means for drawing humidified filtered inlet air or unhumidified filtered inlet air into said first air passage means and for circulating air flow through said hood and said first air passage means.

2. An infant incubator according to claim 1 wherein said humidifying means include a humidifier, first valve means in said second air passage means for conducting filtered inlet air to said humidifier, and second valve means in said second air passage means for conducting humidified filtered inlet air from said humidifier to said first air passage means.

3. An infant incubator according to claim 1 wherein said humidifying means also selectively prevent unhumidified filtered inlet air from being conducted to said first air passage means upon selection.

4. An infant incubator comprising:

a hood;

a base upon which said hood is mounted;

first air passage means extending between first and second openings into said hood for conducting air flow into said hood through said first opening and for conducting air flow leaving said hood through said second opening and to said first opening;

means for supplying inlet air;

second air passage means for conducting inlet air to said first air passage means;

means within said second air passage means for filtering inlet air;

a humidifier;

means upstream from said first air passage means for selectively conducting filtered inlet air to said humidifier and for selectively conducting humidified filtered inlet air from said humidifier or unhumidified filtered inlet air to said first air passage means;

and means within said first air passage means for:

(a) drawing filtered inlet air into said first air passage means when filtered inlet air is not conducted to said humidifier;

(b) drawing humidified filtered inlet air into said first air passage means when filtered inlet air is conducted to said humidifier, and (c) circulating air flow through said hood and said first air passage means.

5. An infant incubator according to claim 4 wherein said selective conducting means include first valve means in said second air passage means for conducting filtered inlet air to said humidifier and second valve means in said second air passage means for conducting humidified filtered inlet air from said humidifier to said first air passage means.

6. An infant incubator according to claim 5 wherein said humidifier includes means for controlling said first and said second valve means.

7. An infant incubator according to claim 4 wherein said selective conducting means also selectively prevent unhumidified filtered inlet air from being conducted to said first air passage means when filtered inlet air is selectively conducted to said humidifier.

8. An infant incubator comprising:

a hood;

a base upon which said hood is mounted;

first air passage means extending between first and second openings into said hood for conducting air flow into said hood through said first opening and for conducting air flow leaving said hood through said second opening and to said first opening;

means for supplying inlet air;

second air passage means for conducting inlet air to said first air passage means;

means within said second air passage means for filtering inlet air;

a humidifier having an inlet port coupling to said humidifier and an outlet port coupling from said humidifier;

first valve means in said second air passage means for selectively conducting filtered inlet air to said humidifier or passing filtered inlet air through said second air passage means in response to engagement of said first valve means by said inlet port coupling to said humidifier;

second valve means in said second air passage means for selectively conducting humidified filtered inlet air from said humidifier or filtered inlet air from said second air passage means to said first air passage means in response to engagement of said second valve means by said outlet port coupling to said humidifier;

and means within said first air passage means for:

(a) drawing filtered inlet air into said first air passage means when filtered inlet air is not conducted to said humidifier;

(b) drawing humidified filtered inlet air into said first air passage means when filtered inlet air is conducted to said humidifier, and (c) circulating air flow through said hood and said first air passage means.

9. An infant incubator comprising:

a hood;

a base upon which said hood is mounted;

first air passage means extending between first and second openings into said hood for conducting air flow into said hood through said first opening and for conducting air flow leaving said hood through said second opening and to said first opening;

means for supplying inlet air;

second air passage means for conducting inlet air to said first air passage means and including:

(a) an air inlet line having spaced apart first and second openings in a wall thereof, and (b) first and second sealing grommets fitted in said first and second openings, respectively;

means within said second air passage means for filtering inlet air;

a humidifier;

first valve means in said second air passage means for selectively conducting filtered inlet air to said humidifier, said first valve means including:

(a) a base fixed in position in said air inlet line, (b) a cap movable transverse to said air inlet line, and (c) a spring urging said cap of said first valve means against said first grommet to seal said first opening in said inlet line;

second valve means in said second air passage means for selectively conducting humidified filtered inlet air from said humidifier to said first air passage means, said second valve means including:
 (a) a base fixed in position in said air inlet line and having an opening through which filtered inlet air flows,
 (b) a cap movable transverse to said air inlet line,
 (c) a spring urging said cap of said second valve means against said second grommet to seal said second opening in said air inlet line, and
 (d) a sealing ring carried by said cap of said second valve means;
and means within said first air passage means for:
 (a) drawing filtered inlet air into said first air passage means when filtered inlet air is not conducted to said humidifier;
 (b) drawing humidified filtered inlet air into said first air passage means when filtered inlet air is conducted to said humidifier, and
 (c) circulating air flow through said hood and said first air passage means.

10. An infant incubator according to claim 9 wherein said humidifier includes means for engaging said cap of said first valve means to control said first valve means and for engaging said cap of said second valve means to control said second valve means.

11. An infant incubator according to claim 9 wherein said humidifier includes:
 (a) an inlet port coupling adapted to engage said cap of said first valve means to move said cap of said first valve means away from said first grommet against the action of said spring of said first valve means, and
 (b) an outlet port coupling adapted to engage said cap of said second valve means to move said cap of said second valve means away from said second grommet against the action of said spring of said second valve means and to move said sealing ring of said second valve means to seal said opening in said base of said second valve means.

12. An infant incubator comprising:
a hood;
a base upon which said hood is mounted;
first air passage means extending between first and second openings into said hood for conducting air flow into said hood through said first opening and for conducting air flow leaving said hood through said second opening and to said first opening;
means for supplying inlet air;
second air passage means through which inlet air flows for conducting air flow to said first air passage means;
means within said second air passage means for filtering inlet air;
a humidifier selectively mounted to said base and having control means upstream from said first air passage means for selectively:
 (a) diverting filtered inlet air from said second air passage means to said humidifier or passing filtered inlet air through said second air passage means to said first air passage means, and
 (b) introducing humidified filtered inlet air to aid first air passage means;
and means within said first air passage means for:
 (a) drawing filtered inlet air into said first air passage means when filtered inlet air is not diverted to said humidifier,
 (b) drawing humidified filtered inlet air into said first air passage means when filtered inlet air is diverted to said humidifier, and
 (c) circulating air flow through said hood and said first air passage means.

13. An infant incubator according to claim 12 further including valve means in said second air passage means engaged by said control means of said humidifier for:
 (a) selectively blocking flow of filtered inlet air through said second air passage means and conducting filtered inlet air to said humidifier when said humidifier is mounted to said base, and
 (b) introducing humidified filtered inlet air to said air passage means when said humidifier is mounted to said first base.

14. An infant incubator according to claim 12 wherein said control means of said humidifier also selectively prevent unhumidified filtered inlet air from being introduced to said first air passage means when filtered inlet air is selectively diverted from said second air passage means to said humidifier.

* * * * *

UNITED STATES PATENT AND TRADEMARK OFFICE
CERTIFICATE OF CORRECTION

PATENT NO. : 5,224,923
DATED : July 6, 1993
INVENTOR(S) : Joseph J. Moffett, et al It is certified that error appears in the above-indentified patent and that said Letters Patent is hereby corrected as shown below:

```
Col. 8, line 19 - delete "aid" and substitute --said--
Col. 8, line 37 - insert "first" between "said" and "air"
Col. 8, line 39 - delete "first"
```

Signed and Sealed this

Twelfth Day of April, 1994

Attest:

BRUCE LEHMAN

Attesting Officer

*Commissioner of Patents and Trademarks*